United States Patent
Takahashi

(10) Patent No.: US 9,039,625 B2
(45) Date of Patent: May 26, 2015

(54) HEAD UNIT, ULTRASONIC PROBE, ELECTRONIC INSTRUMENT, AND DIAGNOSTIC DEVICE

(71) Applicant: SEIKO EPSON CORPORATION, Tokyo (JP)

(72) Inventor: Masaki Takahashi, Chiba (JP)

(73) Assignee: Seiko Epson Corpoation, Tokyo (JP)

( * ) Notice: Subject to any disclaimer, the term of this patent is extended or adjusted under 35 U.S.C. 154(b) by 42 days.

(21) Appl. No.: 13/774,270

(22) Filed: Feb. 22, 2013

(65) Prior Publication Data

US 2013/0225993 A1    Aug. 29, 2013

(30) Foreign Application Priority Data

Feb. 24, 2012  (JP) ................. 2012-038362

(51) Int. Cl.
*A61B 8/14* (2006.01)
*A61B 8/00* (2006.01)
*A61B 8/08* (2006.01)
*B06B 1/06* (2006.01)
*A61B 8/04* (2006.01)

(52) U.S. Cl.
CPC ............ *A61B 8/4444* (2013.01); *A61B 8/4483* (2013.01); *A61B 8/52* (2013.01); *A61B 8/145* (2013.01); *A61B 8/04* (2013.01); *A61B 8/461* (2013.01); *A61B 8/4411* (2013.01); *B06B 1/0629* (2013.01)

(58) Field of Classification Search
CPC ............. A61B 8/00; A61B 8/08; A61B 8/44; A61B 8/4472; A61B 8/4427; A61B 8/4444; A61B 8/4483; A61B 8/52; A61B 8/145; A61B 8/04; A61B 8/461; A61B 8/4411; G10K 11/34; B06B 1/0629
USPC .................................... 600/437–469
See application file for complete search history.

(56) References Cited

U.S. PATENT DOCUMENTS

| | | | |
|---|---|---|---|
| 8,038,619 B2* | 10/2011 | Steinbacher | 600/444 |
| 2009/0012401 A1* | 1/2009 | Steinbacher | 600/459 |
| 2010/0174194 A1* | 7/2010 | Chiang et al. | 600/447 |
| 2010/0249598 A1* | 9/2010 | Smith et al. | 600/459 |
| 2011/0074244 A1* | 3/2011 | Osawa | 310/318 |
| 2012/0179044 A1* | 7/2012 | Chiang et al. | 600/447 |

FOREIGN PATENT DOCUMENTS

JP      2007-142555 A      6/2007

* cited by examiner

*Primary Examiner* — Sanjay Cattungal
(74) *Attorney, Agent, or Firm* — Global IP Counselors, LLP

(57) ABSTRACT

A head unit for an ultrasonic probe includes a connecting section, an element chip and a storing section. The connecting section is configured to electrically connect the head unit to a probe main body of the ultrasonic probe. The element chip includes an ultrasonic element array having a substrate defining a plurality of openings arranged in an array pattern and a plurality of ultrasonic transducer elements with each of the ultrasonic transducer elements being provided in each of the openings. The element chip is configured to be electrically connected to a processing device of the probe main body through the connecting section. The storing section is configured to store operation setting information of the processing device to be output to the processing device through the connecting section.

15 Claims, 10 Drawing Sheets

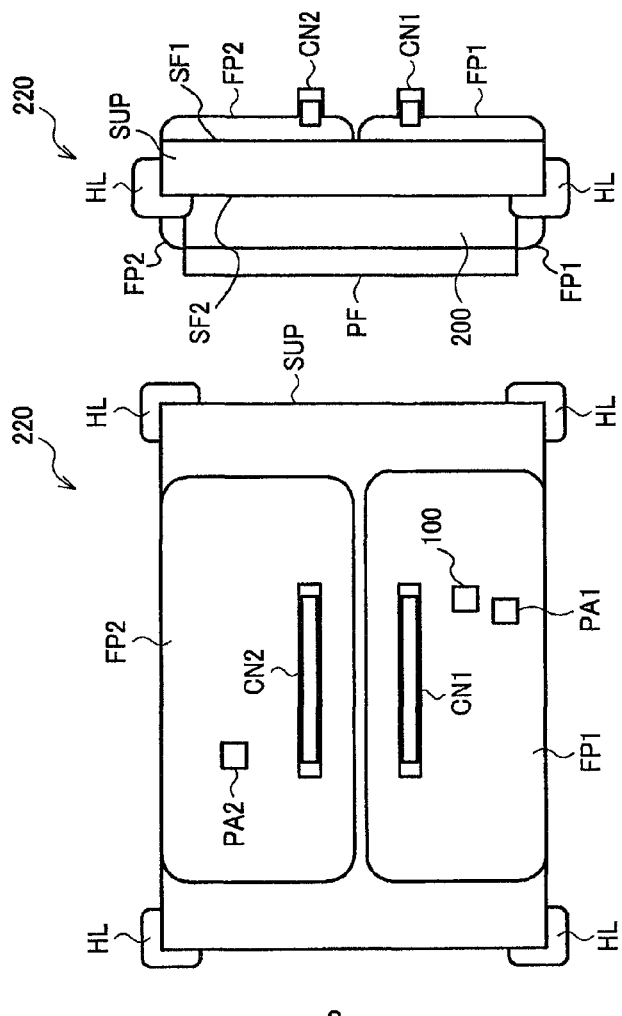
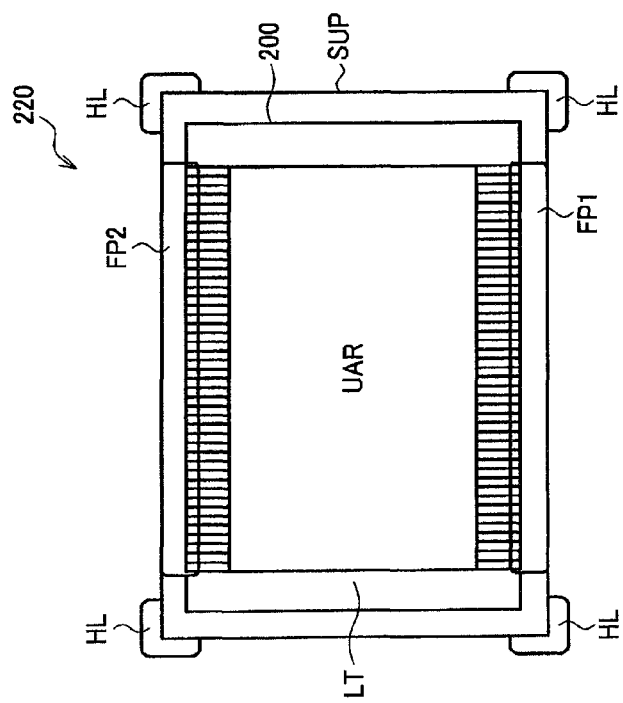
Fig. 6A
Fig. 6B
Fig. 6C

|  | ULTRASONIC DIAGNOSIS IMAGE PROCESSING | BLOOD PRESSURE MEASUREMENT PROCESSING | TARGET CIRCUIT FOR CHANGING SETTINGS |
| --- | --- | --- | --- |
| MEASUREMENT DEPTH | 3 ~ 30 cm | < 1 cm | -- |
| DRIVING FREQUENCY | 3.5 MHz | 10 MHz | TX |
| VOLTAGE MAGNITUDE | 10 V | 20 V | TX |
| SCANNING MODE | SECTOR SCANNING | NO SCANNING | MUX |
| ATTENUATION AMOUNT | VARIABLE | FIXED | VCAT |
| GAIN | 30 dB | 20 dB | PGA |
| INTERCEPTION FREQUENCY | 10 MHz | 15 MHz | LPF |
| RECORDING PERIOD | ~ 40 MHz | 50 MHz | ADC |

Fig. 9

HEAD UNIT, ULTRASONIC PROBE,
ELECTRONIC INSTRUMENT, AND
DIAGNOSTIC DEVICE

CROSS-REFERENCE TO RELATED
APPLICATIONS

This application claims priority to Japanese Patent Application No. 2012-038362 filed on Feb. 24, 2012. The entire disclosure of Japanese Patent Application No. 2012-038362 is hereby incorporated herein by reference.

BACKGROUND

1. Technical Field

The present invention relates to a head unit, an ultrasonic probe, an electronic instrument, and a diagnostic device.

2. Related Art

An ultrasonic diagnostic device for testing the inside of a human body, for example, has been known as a device in which ultrasonic waves are emitted toward a target and reflected waves are received from the boundary between different acoustic impedances inside the target. In Japanese Laid-Open Patent Publication No. 2007-142555, a technique in which ultrasonic beams are emitted by arranging piezoelectric elements in a matrix array pattern has been disclosed as an ultrasonic probe used for an ultrasonic diagnostic device.

This technique, however, has a problem that a user has to configure operation settings of a processing device and the like in the probe in a case where the probe is replaced depending on a different target to be diagnosed.

SUMMARY

According to some aspects of the present invention, a replaceable head unit which can automatically configure operation settings, an ultrasonic probe, an electronic instrument, a diagnostic device, and the like are provided.

According to one aspect of the present invention, a head unit for an ultrasonic probe includes a connecting section, an element chip and a storing section. The connecting section is configured to electrically connect the head unit to a probe main body of the ultrasonic probe. The element chip includes an ultrasonic element array having a substrate defining a plurality of openings arranged in an array pattern and a plurality of ultrasonic transducer elements with each of the ultrasonic transducer elements being provided in each of the openings. The element chip is configured to be electrically connected to a processing device of the probe main body through the connecting section. The storing section is configured to store operation setting information of the processing device to be output to the processing device through the connecting section.

With this aspect, the head unit can be made removable with respect to the probe main body through the connecting section. Further, since the operation settings of the processing device can be configured based on the operation setting information stored in the storing section, operation settings corresponding to the use of the head unit can be configured by attaching the head unit to the probe main body. As a result, operation settings suitable for a different target to be diagnosed, for example, can be automatically configured by replacing the head unit.

According to one aspect of the present invention, the processing device preferably has an analog front-end section configured to perform signal processing to a signal received from the ultrasonic element array, and the storing section is preferably configured to store gain setting information for setting gain of at least one of a low noise amplifier and a programmable gain amplifier of the analog front-end section as the operation setting information.

With this configuration, since the gain of the analog front-end section can be set based on the operation setting information stored in the storing section, the gain can be set corresponding to the use of the head unit.

According to one aspect of the present invention, the storing section is preferably configured to store frequency characteristic setting information for setting frequency characteristics of a low-pass filter of the analog front-end section as the operation setting information.

With this configuration, since the frequency characteristics of the analog front-end section can be set based on the operation setting information stored in the storing section, the frequency characteristics can be set corresponding to the use of the head unit.

According to one aspect of the present invention, the storing section is preferably configured to store the operation setting information corresponding to a probe target of the ultrasonic probe.

With this configuration, since the operation settings corresponding to a probe target of the ultrasonic probe can be configured based on the operation setting information stored in the storing section, operation settings suitable for a different target to be diagnosed, for example, can be automatically configured.

According to one aspect of the present invention, the operation setting information corresponding to the probe target of the ultrasonic probe preferably corresponds to one of ultrasonic diagnosis image processing and blood pressure measurement processing.

With this configuration, the operation setting information corresponding to ultrasonic diagnosis image processing can be stored in a storing section of a first head unit, and the operation setting information corresponding to blood pressure measurement processing can be stored in a second head unit. Consequently, operation settings corresponding to ultrasonic diagnosis image processing can be configured in a case where the first head unit is mounted. Operation settings corresponding to blood pressure measurement processing can be configured in a case where the second head unit is mounted.

According to one aspect of the present invention, the head unit preferably further includes a supporting member supporting the element chip and the storing section.

With this configuration, the element chip and the storing section can be supported by the supporting member in a probe case.

According to one aspect of the present invention, the connecting section preferably has a plurality of connecting terminals connected to the probe main body, the storing section and the connecting terminals are preferably disposed on a first surface side of the supporting member, and the element chip is preferably supported on a second surface side of the supporting member, the second surface being a reverse surface of the first surface of the supporting member.

With this configuration, ultrasonic waves can be emitted from the second surface side on which the element chip is supported. Also, since the first surface side on which the connecting section is disposed can be directed toward the probe main body, ultrasonic waves can be emitted without being interrupted toward the probe main body.

According to one aspect of the present invention, the connecting section preferably has a connector including the connecting terminals and a flexible printed circuit board including wiring connecting the connector and the element chip, and the storing section is preferably disposed in the flexible printed circuit board.

With this configuration, the connector can be disposed on the first surface side of the supporting member, and the connector and the element chip supported on the second surface side of the supporting member can be connected through the flexible printed circuit board. Also, the storing section and the connector can be connected through the flexible printed circuit board. Consequently, the element chip and the storing section can be electrically connected to the probe main body.

According to one aspect of the present invention, an ultrasonic probe includes the probe main body, and the head unit according to the above described aspects with the head unit being removably coupled to the probe main body.

According to one aspect of the present invention, the probe main body preferably includes a processing device having an analog front-end section configured to perform signal processing to a signal received from the ultrasonic element array, a transmitting section configured to output a driving signal to the ultrasonic element array, and a controlling section configured to control the analog front-end section and the transmitting section, the controlling section being configured to set operations of the analog front-end section and the transmitting section based on the operation setting information read out from the storing section of the head unit.

With this configuration, since the operation settings of the analog front-end section and the transmitting section can be configured based on the operation setting information stored in the storing section, operation settings suitable for a different target to be diagnosed, for example, can be automatically configured by replacing the head unit.

According to one aspect of the present invention, an electronic instrument includes the head unit according to the above described aspects.

According to one aspect of the present invention, a diagnostic device includes the head unit according to the above described aspects, and a display section configured to display image data.

BRIEF DESCRIPTION OF THE DRAWINGS

Referring now to the attached drawings which form a part of this original disclosure:

FIG. 6A, FIG. 6B, and FIG. 6C show the details of the second example of the configuration of the head unit.

FIG. 9 shows an example of operation settings corresponding to ultrasonic diagnosis image processing and blood pressure measurement processing.

DETAILED DESCRIPTION OF EXEMPLARY EMBODIMENTS

Next, preferred embodiments of the present invention will be explained in detail. The embodiments explained below shall not be construed as unreasonably limiting the subject matter of the present invention described in the claims, and all the elements explained in the embodiments are not necessarily essential to the solving means of the present invention.

1. Ultrasonic Transducer Element

Figure 1A:
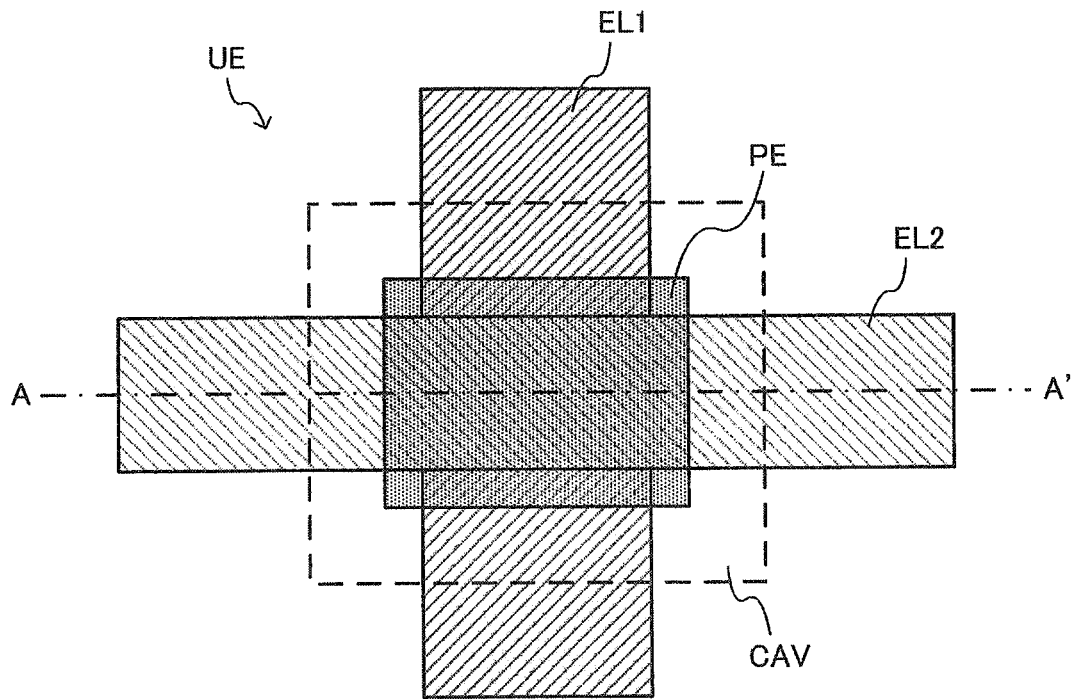
FIG. 1A and FIG. 1B show an example of a basic configuration of an ultrasonic transducer element.
Figure 1B:
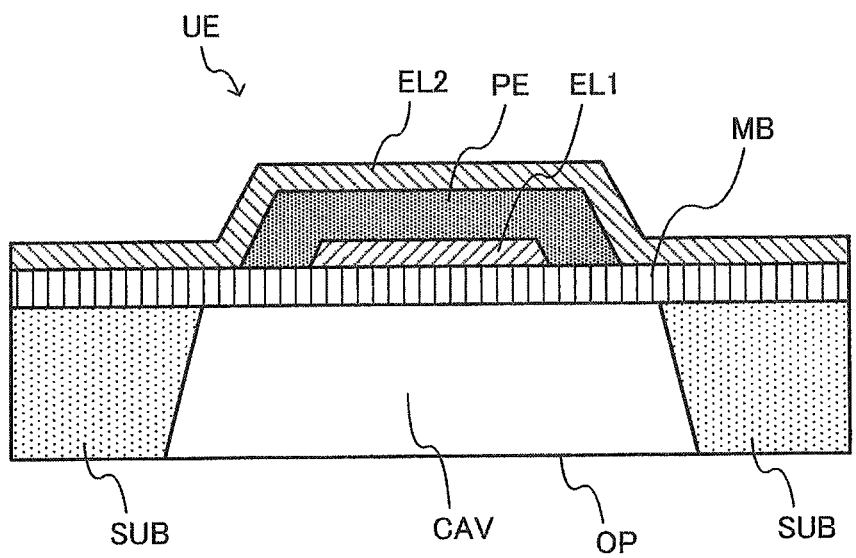

FIG. 1A and FIG. 1B show an example of a basic configuration of an ultrasonic transducer element (ultrasonic element) UE that is included in a head unit according to the present embodiment. The ultrasonic transducer element UE according to the present embodiment includes a first electrode layer EL1, a piezoelectric body layer PE, a second electrode layer EL2, a membrane (supporting member) MB, and a cavity region (cavity section) CAV. The ultrasonic transducer element UE according to the present embodiment is not limited to the configuration of FIG. 1, and various changes and modifications are possible. For example, a part of its components can be omitted or replaced with other components, or other components can be added.

FIG. 1A is a plan view of the ultrasonic transducer element UE formed on a substrate (silicon substrate) SUB, seen from a direction perpendicular to the substrate on a side where the element is formed. FIG. 1B is a sectional view along line A-A' of FIG. 1A.

The first electrode layer EL1 is formed on an upper layer of the membrane MB as a metal thin film, for example. The first electrode layer (lower electrode layer) EL1 may be a wiring extended outside a region in which the element is formed as shown in FIG. 1A, and connected to the adjacent ultrasonic transducer element UE.

The piezoelectric body layer PE is formed of a PZT (piezoelectric zirconate titanate) thin film, for example. The piezoelectric body layer PE is arranged to cover at least a part of the first electrode layer EL1. The material of the piezoelectric body layer PE is not limited to PZT. Lead titanate ($PbTiO_3$), lead zirconate ($PbZrO_3$), lead lanthanum titanate ($(Pb, La)TiO_3$), or the like may be used.

The second electrode layer (upper electrode layer) EL2 is formed of a metal thin film, for example, and is arranged to cover at least a part of the piezoelectric body layer PE. The second electrode layer EL2 may be a wiring extended outside the region in which the element is formed as shown in FIG. 1A, and connected to the adjacent ultrasonic transducer element UE.

The membrane MB is provided on an upper layer of the cavity region CAV with a two-layer configuration made of an $SiO_2$ thin film and a $ZrO_2$ thin film, for example. The membrane MB supports the piezoelectric body layer PE, the first electrode layer EL1 and the second electrode layer EL2. The membrane MB vibrates in accordance with expansion and contraction of the piezoelectric body layer PE so as to generate ultrasonic waves.

The cavity region CAV is formed from a reverse surface (in which no element is formed) of the silicon substrate SUB by etching such as reactive ion etching (RIE). Ultrasonic waves are emitted from an opening OP of the cavity region CAV.

A first electrode of the ultrasonic transducer element UE is formed of the first electrode layer EL1, and a second electrode of the ultrasonic transducer element UE is formed of the second electrode layer EL2. More specifically, a part of the first electrode layer EL1 that is covered by the piezoelectric body layer PE forms the first electrode, and a part of the second electrode layer EL2 that covers the piezoelectric body layer PE forms the second electrode. In other words, the piezoelectric body layer PE is sandwiched by the first electrode and the second electrode.

The piezoelectric body layer PE expands or contracts in an in-plane direction when a voltage is applied between the first electrode and the second electrode, that is, between the first electrode layer EL1 and the second electrode layer EL2. One surface of the piezoelectric body layer PE is attached to the membrane MB through the first electrode layer EL1. Although the second electrode layer EL2 is formed on the other surface of the piezoelectric body layer PE, no other layer is formed on the second electrode layer EL2. Therefore, the piezoelectric body layer PE is difficult to expand or contract on the membrane MB side, and the piezoelectric body layer PE is easy to expand or contract on the second electrode layer EL2 side. Accordingly, when a voltage is applied to the piezoelectric body layer PE, convex warpage occurs on the cavity region CAV side, which causes the membrane MB to warp. When an alternating-current voltage is applied to the piezoelectric body layer PE, the membrane MB vibrates in a film thickness direction, and ultrasonic waves are emitted from the opening OP by the vibration of the membrane MB. The voltage applied to the piezoelectric body layer PE is 10-30 V, for example. The frequency is 1-10 MHz, for example.

2. Element Chip

Figure 2:
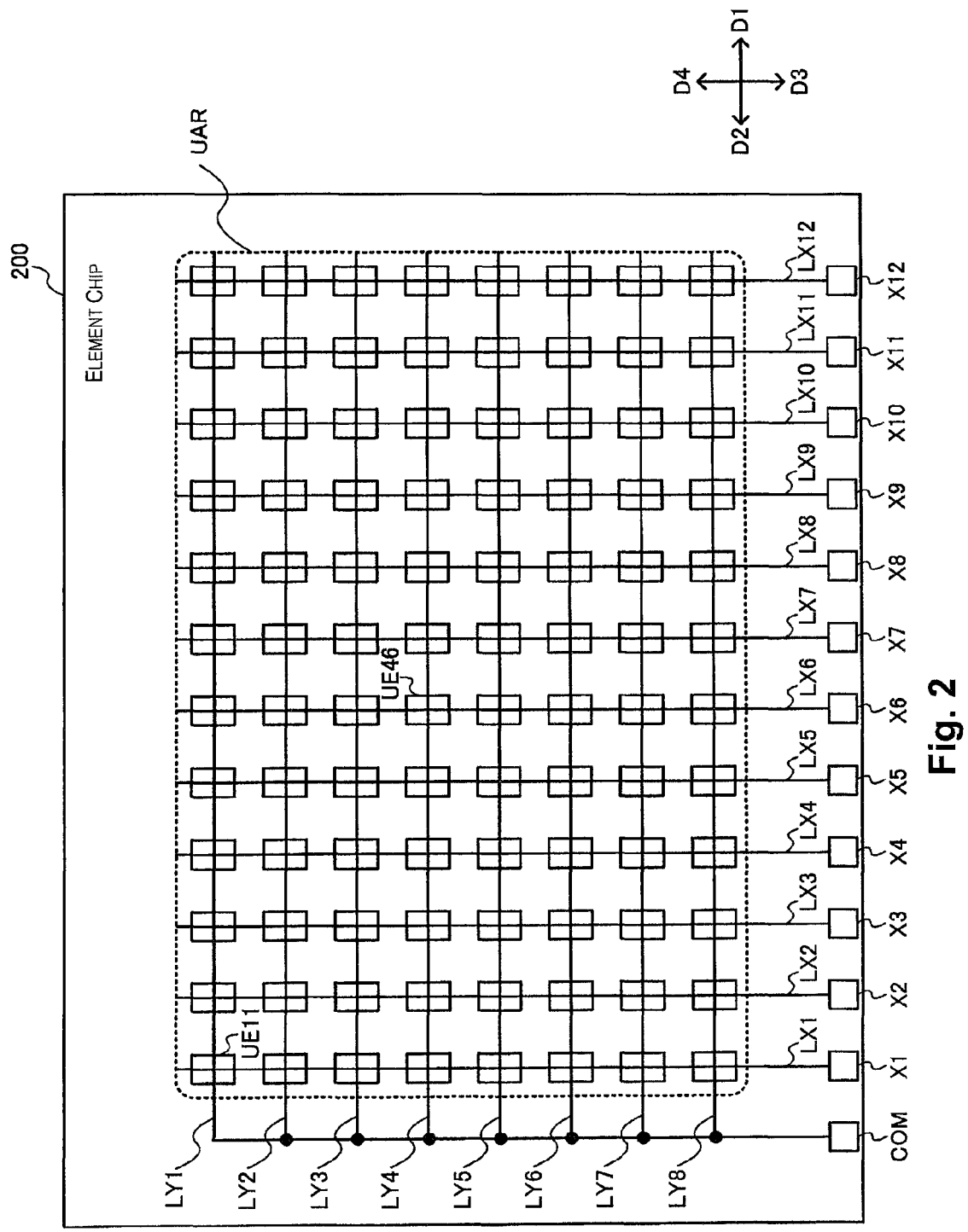
FIG. 2 shows a first example of a configuration of an element chip.

FIG. 2 shows a first example of a configuration of an element chip 200 included in the head unit according to the present embodiment. The element chip 200 of the first example includes an ultrasonic element array UAR. The ultrasonic element array UAR has a substrate in which a plurality of openings are provided in an array pattern, and the plurality of ultrasonic transducer elements UE, each ultrasonic transducer element being provided in each opening of the plurality of openings. The ultrasonic element array UAR further includes first-$n^{th}$ ("n" is an integer of 2 or more) signal lines LX1-LXn, and first-$m^{th}$ ("m" is an integer of 2 or more) common electrode lines LY1-LYm. The element chip 200 further includes first-$n^{th}$ signal terminals X1-Xn and a common terminal COM. FIG. 2 shows a case where "m" is 8 and "n" is 12 as an example, but other values are possible. The element chip 200 according to the present embodiment is not limited to the configuration of FIG. 2, and various changes and modifications are possible. For example, a part of its components can be omitted or replaced with other components, or other components can be added.

The ultrasonic element array UAR includes the plurality of ultrasonic transducer elements (ultrasonic element) UE provided in a matrix array pattern (array pattern in a broad sense) of "m" rows and "n" columns, for example. The ultrasonic transducer elements UE can be configured as shown in FIGS. 1A and 1B. More specifically, as shown in FIG. 2, the ultrasonic transducer elements UE of first-eighth ($m^{th}$ in a broad sense) rows are arranged in a third direction D3, and the ultrasonic transducer elements UE of first-twelfth ($n^{th}$ in a broad sense) columns are arranged in a first direction D1 perpendicular to the third direction D3. In the following explanations, in order to specify a position of the ultrasonic transducer element UE in the array, the ultrasonic transducer element UE positioned in the fourth row and the sixth column is described as UE46, for example.

The arrangement of the ultrasonic transducer element (ultrasonic element) UE is not limited to the matrix pattern of "m" rows and "n" columns shown in FIG. 2. For example, the so-called zigzag pattern in which an "m" number of ultrasonic transducer elements are arranged in an odd number column and an "m−1" number of ultrasonic transducer elements are arranged in an even number column may be used.

The first-eighth ($m^{th}$ in a broad sense) common electrode lines LY1-LY8 are arranged along the first direction D1 or a second direction D2 in the ultrasonic element array UAR. The $i^{th}$ common electrode line LYi ("i" is an integer satisfying 1≤i≤8) of the first-eighth common electrode lines LY1-LY8 is connected to one of the first electrode and the second electrode of each ultrasonic transducer element UE arranged in the $i^{th}$ row of the ultrasonic element array UAR.

The first-twelfth ($n^{th}$ in a broad sense) signal lines LX1-LX12 are arranged along the third direction D3 or a fourth direction D4 in the ultrasonic element array UAR. The $j^{th}$ signal line LXj ("j" is an integer satisfying 1≤j≤12) of the first-twelfth signal lines LX1-LX12 is connected to the other of the first electrode and the second electrode of each ultrasonic transducer element UE arranged in the $j^{th}$ column of the ultrasonic element array UAR.

Specifically, for example, regarding the ultrasonic transducer element UE11 shown in FIG. 2, the first electrode is connected to the signal line LX1, and the second electrode is connected to the common electrode line LY1. Also, for example, regarding the ultrasonic transducer element UE46 shown in FIG. 2, the first electrode is connected to the sixth signal line LX6, and the second electrode is connected to the fourth common electrode line LY4.

The first-twelfth signal terminals X1-X12 ($n^{th}$ in a broad sense) are arranged on a side of the third direction D3 of the element chip 200, for example, and the first-twelfth signal lines LX1-LX12 are connected thereto. During a transmission period of emitting ultrasonic waves, a driving signal for driving the ultrasonic transducer element UE is input to the signal terminals X1-X12. During a reception period of receiving an ultrasonic echo signal, a received signal from the ultrasonic transducer element UE is output from the signal terminals X1-X12.

The common terminal COM is arranged on a side of the third direction D3, for example, and the first-eighth common electrode lines LY1-LY8 are commonly connected thereto. A common voltage is supplied to the common terminal COM. It is sufficient that the common voltage is a predetermined direct voltage, and it is not necessary to be 0V, that is, a ground potential.

Figure 3:
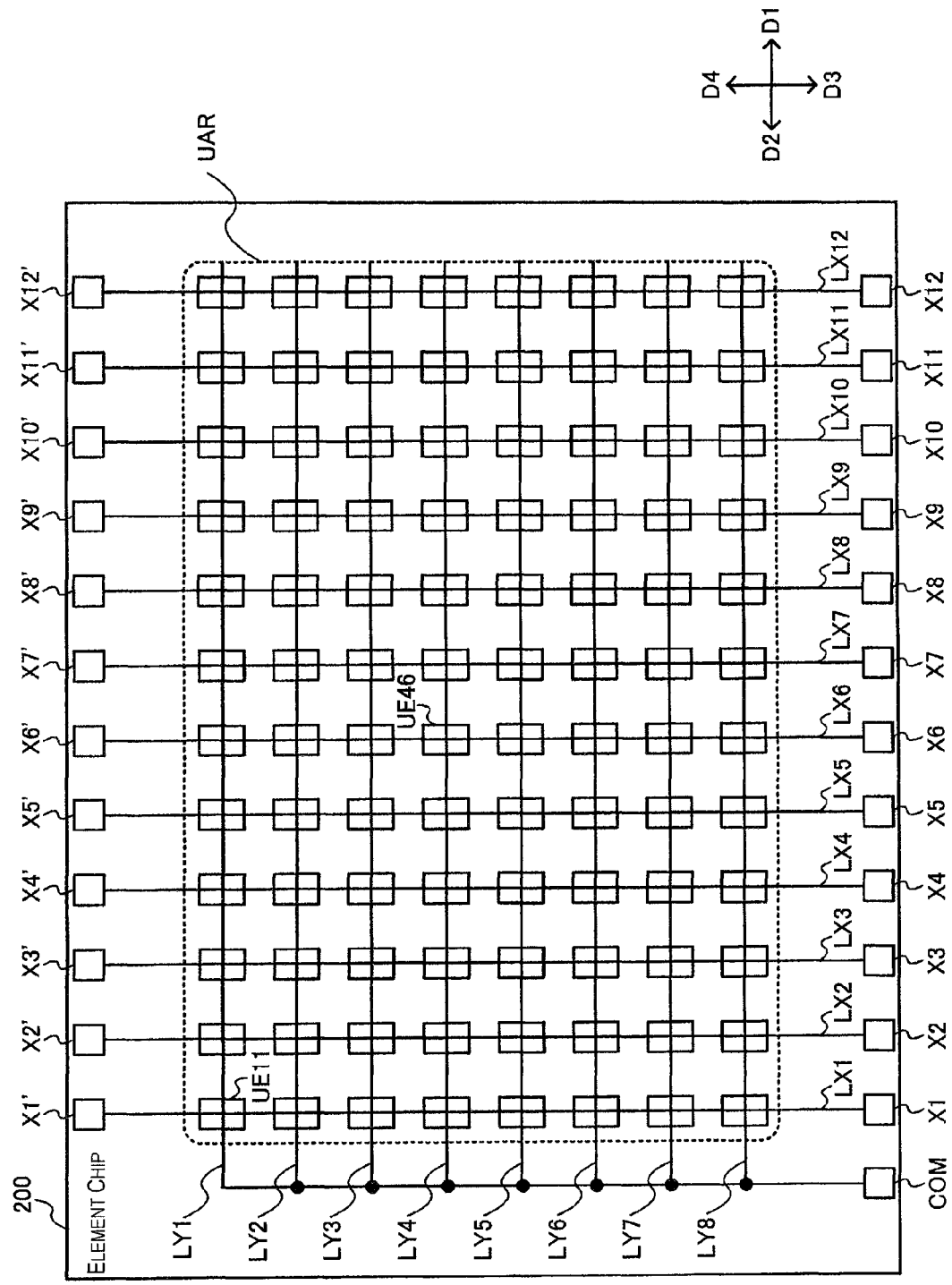
FIG. 3 shows a second example of the configuration of the element chip.

FIG. 3 shows a second example of the configuration of the element chip 200 included in the head unit according to the present embodiment. The element chip 200 of the second example includes the ultrasonic element array UAR, the first-$n^{th}$ ("n" is an integer of 2 or more) signal lines LX1-LXn, the first-$m^{th}$ ("m" is an integer of 2 or more) common electrode lines LY1-LYm, the first-$n^{th}$ signal terminals X1-Xn (first group of chip terminals in a broad sense) on a first side, first-$n^{th}$ signal terminals X1'-Xn' (second group of chip terminals in a broad sense) on a second side, and the common terminal COM. FIG. 3 shows a case where "m" is 8 and "n" is 12 as an example, but other values are possible. The element chip 200 according to the present embodiment is not limited to the configuration of FIG. 3, and various changes and modifications are possible. For example, a part of its components can be omitted or replaced with other components, or other components can be added.

The ultrasonic element array UAR, the first-eighth ($m^{th}$ in a broad sense) common electrode lines LY1-LY8, and the common terminal COM are similar to those of the first example (FIG. 2). Here, therefore, the detailed explanations are omitted.

The first-twelfth ($n^{th}$ in a broad sense) signal lines LX1-LX12 are arranged along the third direction D3 or the fourth direction D4 in the ultrasonic element array UAR. One ends of the signal lines LX1-LX12 are connected to the signal terminals X1-X12 arranged on a side of the first side (side on the third direction D3 side) of the element chip 200, and the other ends are connected to the signal terminals X1'-X12' arranged on a side of the second side (side on the fourth direction D4 side) of the element chip 200 opposite to the first side.

The first-twelfth ($n^{th}$ in a broad sense) signal terminals X1-X12 on the side of the first side are arranged on the side of the first side (side on the third direction D3 side) of the element chip 200, and one ends of the signal lines LX1-LX12 are connected thereto. The first-$n^{th}$ signal terminals X1'-Xn' on the side of the second side are arranged on the side of the second side (side on the fourth direction D4 side) of the element chip 200 opposite to the first side, and the other ends of the signal lines LX1-LX12 are connected thereto.

A driving signal for driving the plurality of ultrasonic transducer element UE is input to the signal terminals X1-X12 arranged on the side of the first side of the element chip 200 and the signal terminals X1'-X12' arranged on the side of the second side of the element chip 200. With this, compared to a case where a driving signal is input to only one end of the signal lines LX1-LX12, decrease in the driving signal voltage due to the wiring resistance of the signal lines LX1-LX12 can be reduced, and thus higher radiation intensity (radiated sound pressure) can be obtained.

The element chip 200 of the present embodiment was explained with reference to FIG. 2 and FIG. 3, but the arrangement of the signal terminals and the common terminal is not limited to one shown in FIG. 2 and FIG. 3. For example, the common terminal may be arranged on the first direction D1 side of the signal terminals X1-X12, or may be arranged on the first direction D1 side or on the second direction D2 side of the signal terminals X1'-X12' on the side of the second side.

3. Head Unit

Figure 4:
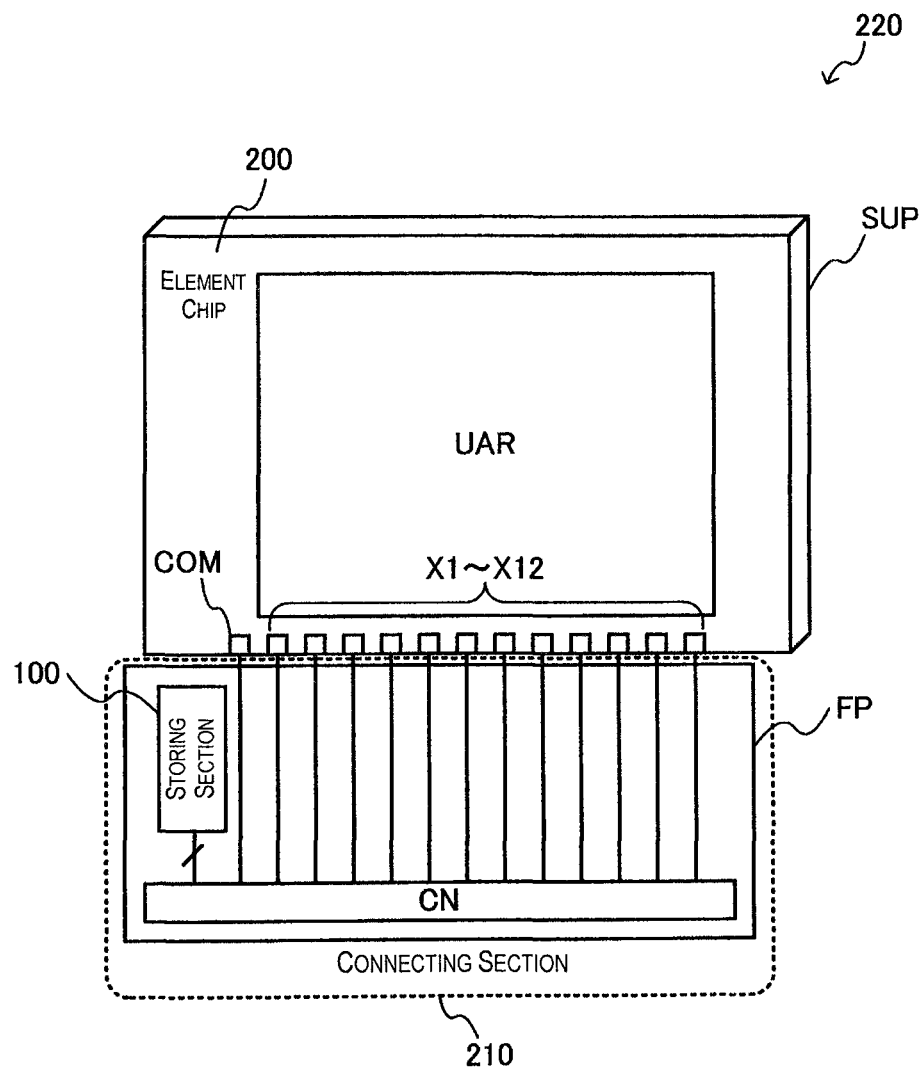
FIG. 4 shows a first example of a configuration of a head unit.

FIG. 4 shows a first example of a configuration of a head unit 220 according to the present embodiment. The head unit 220 of the first example includes the element chip 200, a connecting section 210, a storing section 100, and a supporting member SUP. The head unit 220 according to the present embodiment is not limited to the configuration of FIG. 4, and various changes and modifications are possible. For example, a part of its components can be omitted or replaced with other components, or other components can be added.

As for the element chip 200, the element chip of the first example shown in FIG. 2 can be used. As described above, the element chip 200 includes the ultrasonic element array UAR, the signal lines LX1-LX12, the common electrode lines LY1-LY8, the signal terminals X1-X12, and the common terminal COM. The element chip 200 is electrically connected to a processing device of a probe main body through the connecting section 210.

The connecting section 210 electrically connects the probe main body and the head unit 220. The connecting section 210 has a connector CN that has a plurality of connecting terminals connected to the probe main body, and a flexible printed circuit board FP on which a wiring connecting the connector CN and the element chip 200 is formed. With the connecting section 210, the probe main body and the head unit 220 can be electrically connected, and the head unit 220 can be removable with respect to the probe main body.

The connector CN has the plurality of connecting terminals connected to the signal terminals X1-X12 and the common terminal COM through the wiring formed on the flexible printed circuit board FP, and a memory connecting terminal connected to a memory terminal (not shown in the drawing) of the storing section 100.

The storing section 100 is disposed on the flexible printed circuit board FP, and stores operation setting information of the processing device to be output to the processing device through the connecting section 210. The storing section 100 has the memory terminal (not shown in the drawing), and the memory terminal is connected to the memory connecting terminal of the connector CN through the wiring formed on the flexible printed circuit board FP. The processing device configures settings on processing of transmitting and receiving ultrasonic waves based on the operation setting information read out from the storing section 100. The details of the processing device and the operation setting information will be described later.

The supporting member SUP is a member for supporting the element chip 200 and the storing section 100. As described below, the storing section 100 and a plurality of connecting terminals are arranged on a first surface side of the supporting member SUP. The element chip 200 is supported on a second surface side of the supporting member SUP. The second surface is a reverse surface of the first surface. The detailed configurations of the element chip 200, the connecting section 210, and the supporting member SUP will be described later.

Figure 5:
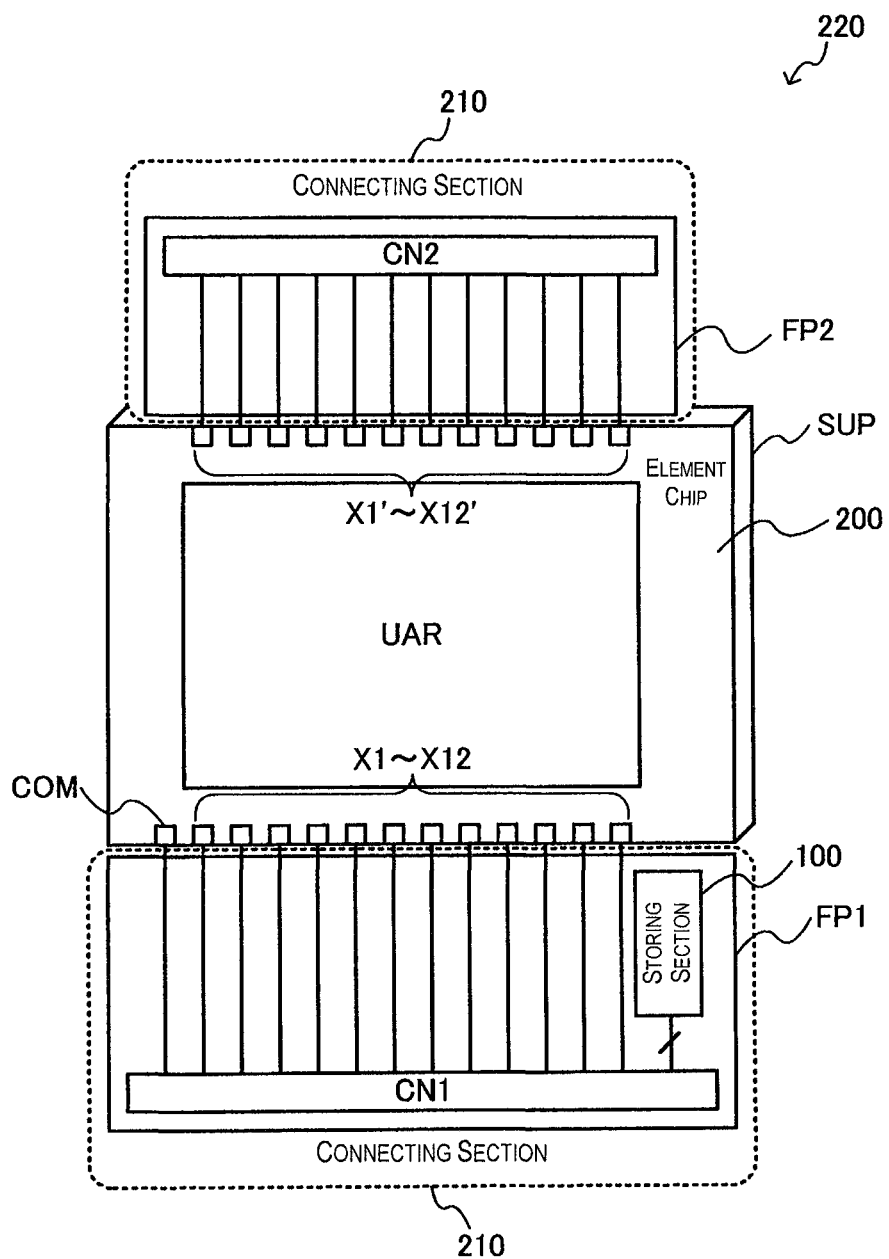
FIG. 5 shows a second example of the configuration of the head unit.

FIG. 5 shows a second example of the configuration of the head unit 220 according to the present embodiment. The head unit 220 of the second example includes the element chip 200, the connecting section 210, the storing section 100, and the supporting member SUP. The head unit 220 according to the present embodiment is not limited to the configuration of FIG. 5, and various changes and modifications are possible. For example, a part of its components can be omitted or replaced with other components, or other components can be added.

As for the element chip 200, the element chip of the second example shown in FIG. 3 can be used. As described above, the element chip 200 includes the ultrasonic element array UAR, the signal lines LX1-LX12, the common electrode lines LY1-LY8, the signal terminals X1-X12 (first group of chip terminals in a broad sense), the signal terminals X1'-X12' (second group of chip terminals in a broad sense), and the common terminal COM. The element chip 200 is electrically connected to the processing device of the probe main body through the connecting section 210.

The connecting section 210 electrically connects the probe main body and the head unit 220. The connecting section 210 has the connector CN that has the plurality of connecting terminals, and the flexible printed circuit board FP on which the wiring connecting the connector CN and the element chip 200 is formed. Specifically, the connecting section 210 has a first connector CN1 and a second connector CN2 as the connector, and also has a first flexible printed circuit board FP1 and a second flexible printed circuit board FP2 as the flexible printed circuit board.

In the first flexible printed circuit board FP1, there is provided a first group of wirings that connects the first group of chip terminals X1-X12 on the side of the first side (side on the third direction D3 side in FIG. 3) of the element chip 200 to the first connector CN1. Also, in the second flexible printed circuit board FP2, there is provided a second group of wirings that connects the second group of chip terminals X1'-X12' arranged on the side of the second side (side on the fourth direction D4 side in FIG. 3) of the element chip 200 opposite to the first side to the second connector CN2.

The connector CN1 has the plurality of connecting terminals where a signal of the first group of chip terminals X1-X12 is input or output through the first group of wirings formed on the flexible printed circuit board FP1, and the memory connecting terminal where a signal of the memory terminal (not shown in the drawing) of the storing section 100 is input or output. The connector CN2 has the plurality of connecting terminals where a signal of the second group of chip terminals X1'-X12' is input or output through the second group of wirings formed on the flexible printed circuit board FP2.

The connecting section 210 is not limited to the configuration of FIG. 5. The connecting section 210 may have a first group of connecting terminals where a signal of the first group of chip terminals arranged on the side of the first side of the element chip 200 is input or output, and a second group of connecting terminals where a signal of the second group of chip terminals arranged on the side of the second side of the element chip 200 opposite to the first side is input or output.

With the connecting section 210, the probe main body and the head unit 220 can be electrically connected, and the head unit 220 can be removable with respect to the probe main body.

The storing section 100 is disposed on the flexible printed circuit board FP1, and stores the operation setting information of the processing device of the probe main body to be output to the processing device through the connecting section 210. The storing section 100 has the memory terminal (not shown in the drawing), and the memory terminal is connected to the memory connecting terminal of the connector CN1 through the first group of wirings formed on the flexible printed circuit board FP1. The processing device configures settings on processing of transmitting and receiving ultrasonic waves based on the operation setting information read out from the storing section 100. The details of the processing device and the operation setting information will be described later.

The storing section 100 may be disposed on the second flexible printed circuit board FP2, and the memory terminal may be connected to the memory connecting terminal of the connector CN2 through the second group of wirings formed on the flexible printed circuit board FP2.

The supporting member SUP is a member for supporting the element chip 200 and the storing section 100. As described below, the storing section 100 and the plurality of connecting terminals are arranged on the first surface side of the supporting member SUP. The element chip 200 is supported on the second surface side of the supporting member SUP. The second surface is a reverse surface of the first surface. The detailed configurations of the element chip 200, the connecting section 210, and the supporting member SUP will be described later.

FIG. 6A, FIG. 6B, and FIG. 6C show the details of the second example of the configuration of the head unit 220 according to the present embodiment. FIG. 6A shows the second surface SF2 side of the supporting member SUP, FIG. 6B shows the first surface SF1 side of the supporting member SUP, and FIG. 6C shows a side surface side of the supporting member SUP. The head unit 220 according to the present embodiment is not limited to the configuration of FIG. 6A, FIG. 6B, and FIG. 6C, and various changes and modifications are possible. For example, a part of its components can be omitted or replaced with other components, or other components can be added.

The connectors CN1, CN2 (connecting terminals in a broad sense) and the storing section 100 are arranged on the first surface SF1 side of the supporting member SUP. One ends of the flexible printed circuit boards FP1, FP2 are connected to the connectors CN1, CN2, respectively. The storing section 100 is provided on the flexible printed circuit board FP1. Circuits such as preamplifiers PA1, PA2 may be provided on the flexible printed circuit boards FP1, FP2. The connectors CN1, CN2 are configured to be removable with respect to the corresponding connectors of the probe main body.

The element chip 200 is supported on the second surface SF2 side of the supporting member SUP. The second surface SF2 is a reverse surface of the first surface SF1. The other ends of the flexible printed circuit boards FP1, FP2 are connected to the terminals of the element chip 200. A fixing member HL is provided in each corner portion of the supporting member SUP, and is used for fixing the head unit 220 to a probe case.

The first surface side of the supporting member SUP refers to a normal direction side of the first surface SF1 of the supporting member SUP, and the second surface side of the supporting member SUP refers to a normal direction side of the second surface SF2 that is a reverse surface of the first surface SF1 of the supporting member SUP. The expression that "provided on the first (second) surface side" includes "provided in contact with the first surface SF1 (the second surface SF2)" and "provided through another member".

As shown in FIG. 6C, a protective member (protective film) PF for protecting the element chip 200 is provided in a reverse surface of the element chip 200 (surface in which the opening OP is provided in FIG. 1B).

4. Ultrasonic Probe

Figure 7A:
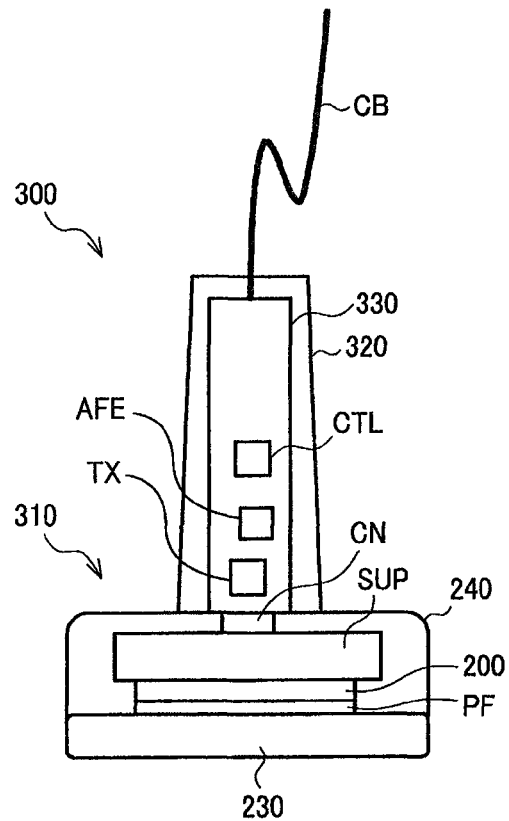
FIG. 7A and FIG. 7B show an example of a configuration of an ultrasonic probe.
Figure 7B:
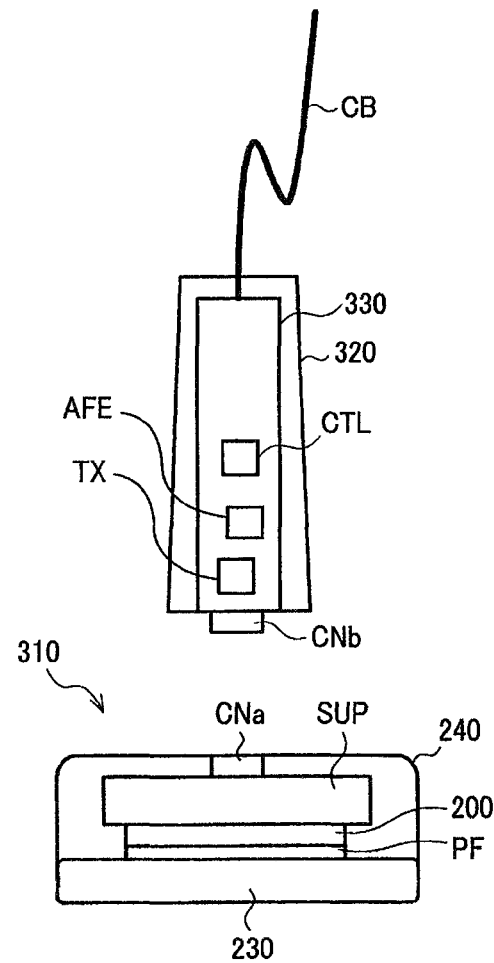

FIG. 7A and FIG. 7B show an example of a configuration of an ultrasonic probe 300 according to the present embodiment. FIG. 7A shows a case where a probe head 310 is mounted to a probe main body 320, and FIG. 7B shows a case where the probe head 310 is separated from the probe main body 320.

The probe head 310 includes the head unit 220, a contact member 230 that contacts a material to be tested, and a probe case 240 for storing the head unit 220. The element chip 200 is provided between the contact member 230 and the supporting member SUP.

The probe main body 320 has a processing device 330 and a probe main body side connector CNb. The processing device 330 has a transmitting section TX, an analog front-end section AFE, and a controlling section CTL. Based on control of the controlling section CTL, the transmitting section TX conducts processing of transmitting a driving signal for driving the ultrasonic transducer element, and the analog front-end section AFE conducts processing of receiving an ultrasonic echo signal (received signal) from the ultrasonic transducer element.

The controlling section CTL controls the transmitting section TX and the analog front-end section AFE. Specifically, the controlling section CTL sets operations of the transmitting section TX and the analog front-end section AFE based on the operation setting information read out from the storing section 100. The probe main body side connector CNb is connected to a head unit (or probe head) side connector CNa.

The probe main body 320 is connected to a main electronic instrument (for example, ultrasonic diagnostic device) through a cable CB.

Although the head unit 220 is stored in the probe case 240, the head unit 220 can be removed from the probe case 240. With this, only the head unit 220 can be replaced. It is also possible to replace in a state of being stored in the probe case 240, that is, as the probe head 310.

Figure 8:
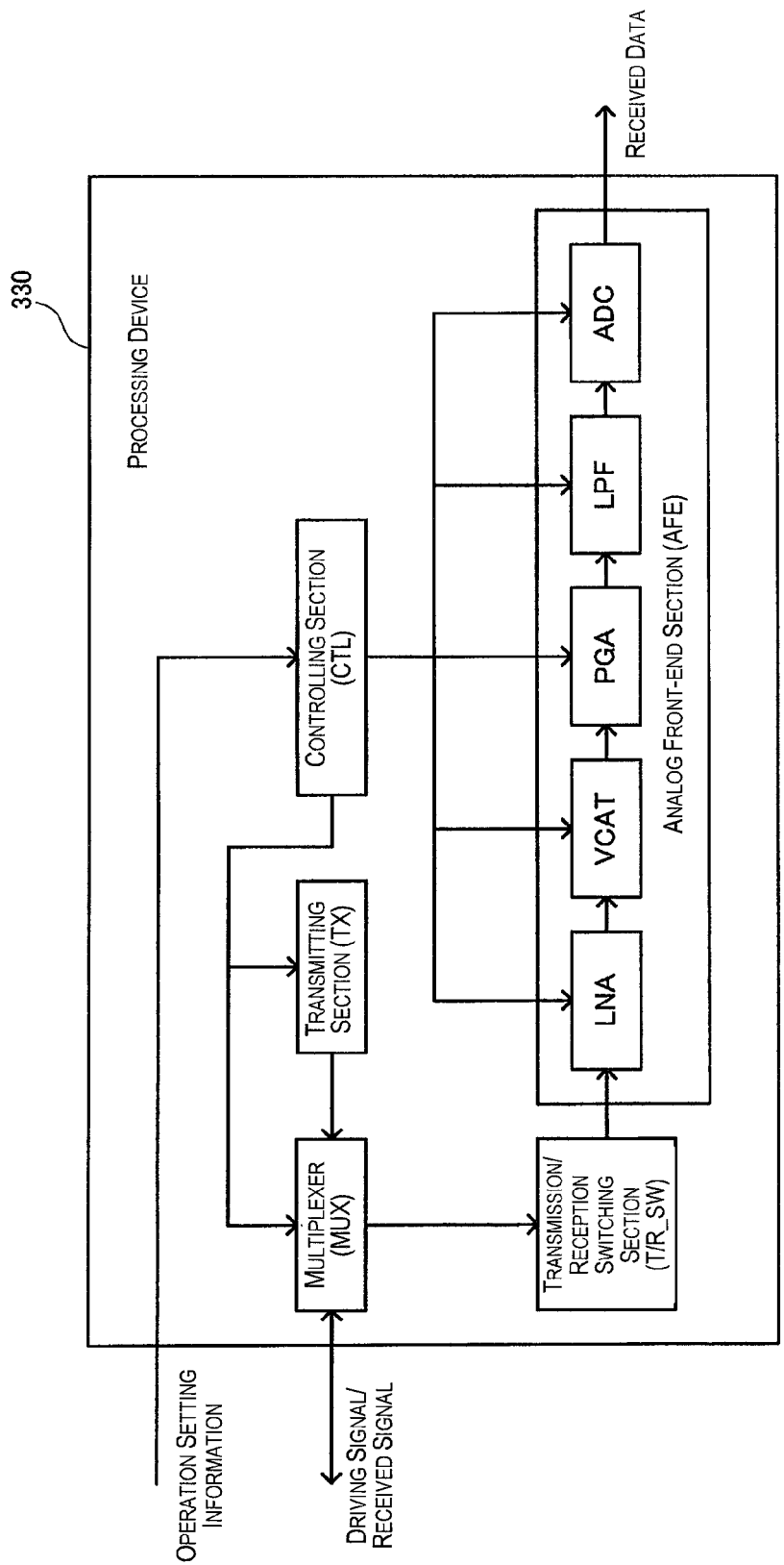
FIG. 8 shows an example of a basic configuration of a processing device.

FIG. 8 shows an example of a basic configuration of the processing device 330 according to the present embodiment. The processing device 330 has the transmitting section TX, the analog front-end section AFE, a multiplexer MUX, a transmission/reception switching section T/R_SW, and the controlling section CTL. The processing device 330 according to the present embodiment is not limited to the configuration of FIG. 8, and various changes and modifications are possible. For example, a part of its components can be omitted or replaced with other components, or other components can be added.

During a transmission period, the transmitting section TX generates a driving signal (pulse) for driving the ultrasonic transducer element UE and outputs the driving signal to the ultrasonic element array UAR based on control of the controlling section CTL. The frequency and the voltage of the driving signal can be set by the controlling section CTL.

The multiplexer MUX conducts channel switching for distributing the driving signal output from the transmitting section TX to each of the signal lines LX1-LX 12.

The transmission/reception switching section T/R_SW makes the multiplexer MUX and the analog front-end section AFE disconnected during a transmission period, and makes the multiplexer MUX and the analog front-end section AFE connected during a reception period. Consequently, a driving signal can be prevented from being input to the analog front-end section AFE during a transmission period, and a received signal (ultrasonic echo signal) can be input to the analog front-end section AFE during a reception period.

The analog front-end section AFE conducts processing of receiving a signal from the ultrasonic element array UAR. The analog front-end section AFE includes a low noise amplifier LNA, a voltage control attenuator VCAT, a programmable gain amplifier PGA, a low-pass filter LPF, and an analog-digital converter ADC. A received signal from the ultrasonic element array UAR is amplified by the low noise amplifier LNA, and is adjusted to be an appropriate signal level by the voltage control attenuator VCAT and the programmable gain amplifier PGA. After an unnecessary frequency component is removed by the low-pass filter LPF, the signal is converted into digital data by the analog-digital converter ADC and output as received data.

The gain of the low noise amplifier LNA and the programmable gain amplifier PGA can be set by the controlling section CTL. Further, the attenuation amount of the voltage control attenuator VCAT, the frequency characteristics (for example, cutoff frequency) of the low-pass filter LPF, and the sampling clock frequency of the analog-digital converter ADC can be set by the controlling section CTL.

The controlling section CTL sets the operations of the analog front-end section AFE and the transmitting section TX based on the operation setting information read out from the storing section 100 of the head unit 220. The storing section 100 stores gain setting information that sets the gain of at least one of the low noise amplifier LNA and the programmable gain amplifier PGA of the analog front-end section AFE as the operation setting information. The controlling section CTL sets the gain of at least one of the low noise amplifier LNA and the programmable gain amplifier PGA based on the gain setting information read out from the storing section 100. The storing section 100 stores frequency characteristic setting information that sets the frequency characteristics of the low-pass filter LPF of the analog front-end section AFE as the operation setting information. The controlling section CTL sets the frequency characteristics (for example, cutoff frequency) of the low-pass filter LPF based on the frequency characteristic setting information read out from the storing section 100. The controlling section CTL can be implemented by an FPGA (Field-Programmable Gate Array) or a CPLD (Complex Programmable Logic Device), for example.

The storing section 100 can store the operation setting information corresponding to a probe target of the ultrasonic probe 300. Specifically, the operation setting information corresponding to a probe target is operation setting information corresponding to ultrasonic diagnosis image processing or operation setting information corresponding to blood pressure measurement processing. More specifically, operation setting information corresponding to ultrasonic diagnosis image processing can be stored in the storing section 100 of the first head unit 220, and operation setting information corresponding to blood pressure measurement processing can be stored in the storing section 100 of the second head unit 220. Consequently, in a case where the first head unit is attached, the controlling section CTL can set the operations of the analog front-end section AFE and the transmitting section TX corresponding to ultrasonic diagnosis image processing. In a case where the second head unit is attached, the controlling section CTL can set the operations of the analog front-end section AFE and the transmitting section TX corresponding to blood pressure measurement processing.

As described above, according to the head unit and the ultrasonic probe of the present embodiment, the operation setting information corresponding to a probe target can be stored in the storing section 100, and the operation settings of transmission processing and reception processing can be configured based on the operation setting information. Therefore, operation settings suitable for the use (target to be diagnosed) of the attached head unit can be automatically configured when the head unit is replaced.

The storing section 100 may store, for example, ID information (manufacturing information) of the element chip 200 or usage history of the head unit as well as the operation setting information. This can achieve appropriate maintenance or quality assurance.

FIG. 9 shows an example of operation settings corresponding to ultrasonic diagnosis image processing (ultrasonic echo image processing) and blood pressure measurement processing.

As shown in FIG. 9, since the measurement depth is as large as 3-30 cm in ultrasonic diagnosis image processing, ultrasonic waves are transmitted at a driving frequency of 3.5 MHz, for example. In order to obtain an echo image, the scanning mode is set to be sector scanning. When an echo is received, the receiving sensitivity corresponding to the measurement depth can be obtained by changing the attenuation amount with respect to the measurement time. Also, both of high display quality of an echo image and low power consumption can be achieved by adjusting the sampling clock frequency in the analog-digital converter ADC to be around 40 MHz.

On the other hand, in blood pressure measurement processing, the blood flow is measured at a shallow location of 1 cm or less from the surface layer in a part for blood pressure measurement such as a wrist. In order to capture the movement of a blood vessel whose diameter is around several millimeters, the resolution is obtained by adjusting the driving frequency as high as around 10 MHz. In this instance, since the length of penetration into the inside of a body becomes small due to the high frequency of ultrasonic waves, the voltage magnitude is increased to be around 20 V. Unlike in the case of displaying an echo image, the data update interval may be long. Therefore, the transmission interval of ultrasonic waves can be made long. In the reception, since the position of the blood vessel does not change, there is no need to make the attenuation amount variable. In order to measure the time change of the blood vessel diameter in detail, the sampling clock frequency in the analog-digital converter ADC is adjusted to be around 50 MHz.

The driving frequency and the voltage magnitude are set by the operation settings of the transmitting section TX configured by the controlling section CTL based on the operation setting information stored in the storing section 100. Similarly, the scanning mode is adjusted by the operation settings of the multiplexer MUX, the attenuation amount is adjusted by the operation settings of the voltage control attenuator VCAT, the gain is adjusted by the operation settings of the programmable gain amplifier PGA, the interception frequency is adjusted by the operation settings of the low-pass filter LPF, and the sampling clock frequency is adjusted by the operation settings of the analog-digital converter ADC.

5. Electronic Instrument

Figure 10:
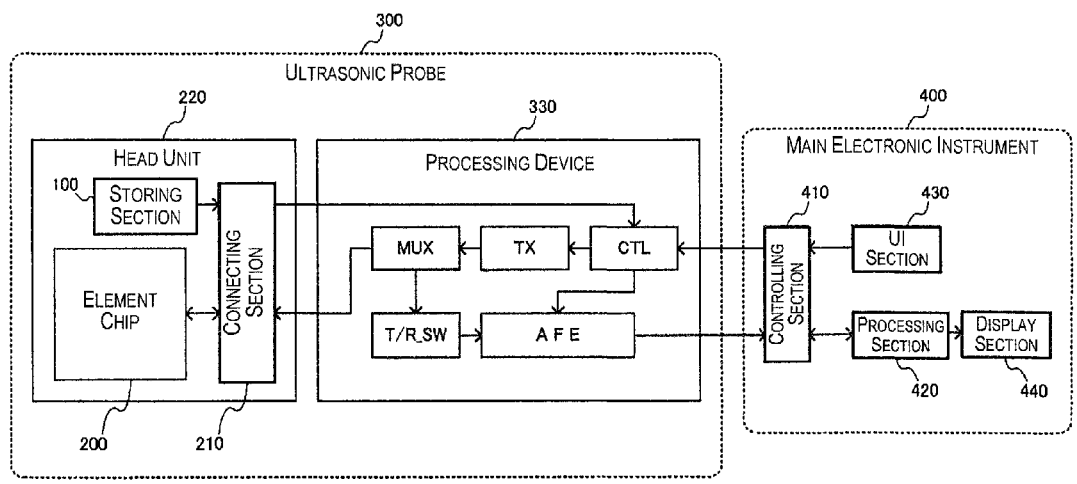
FIG. 10 shows an example of a basic configuration of an electronic instrument.

FIG. 10 shows an example of a basic configuration of an electronic instrument (diagnostic device) that includes the head unit 220 of the present embodiment. The electronic instrument includes the ultrasonic probe 300 and a main electronic instrument 400. The main electronic instrument 400 includes a controlling section 410, a processing section 420, a UI (user interface) section 430, and a display section 440.

The controlling section 410 controls processing of receiving and transmitting ultrasonic waves together with the controlling section CTL of the processing device 330. Further, the controlling section 410 conducts control such as image processing of detected data to the processing section 420. The processing section 420 receives data from the analog front-end section AFE, and conducts necessary processing such as image processing or generation of image data for display. The UI (user interface) section 430 outputs a necessary order (command) to the controlling section 410 based on an operation conducted by a user (for example, an operation to a touch panel). The display section 440 is a liquid crystal display or the like that displays image data for display from the processing section 420.

Part of processing conducted by the controlling section CTL of the processing device 330 may be conducted by the controlling section 410 of the main electronic instrument 400. Part of processing conducted by the controlling section 410 of the main electronic instrument 400 may be conducted by the controlling section CTL of the processing device 330.

As described above, with the head unit, the ultrasonic probe, the electronic instrument, and the diagnostic device according to the present embodiment, operation settings suitable for the use of an attached head unit can be automatically configured. Therefore, in a case where a head unit for ultrasonic diagnosis is attached, for example, operation settings suitable for ultrasonic diagnosis image processing are configured, and the electronic instrument operates as an ultrasonic diagnostic device. Also, in a case where a head unit for blood pressure measurement is attached, for example, operation settings suitable for blood pressure measurement processing are configured, and the electronic instrument operates as a blood pressure measurement device.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the head unit, the ultrasonic probe, the electronic instrument, and the diagnostic device are not limited to the present embodiment, and various changes and modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A head unit for an ultrasonic probe comprising:
a connecting section configured to electrically connect the head unit to a probe main body of the ultrasonic probe;
an element chip including an ultrasonic element array having a substrate defining a plurality of openings arranged in an array pattern and a plurality of ultrasonic transducer elements, each of the ultrasonic transducer elements being provided in each of the openings, the element chip being configured to be electrically connected to a processing device of the probe main body through the connecting section; and
a storing section configured to store a gain setting information including a value of gain of a programmable gain amplifier as operation setting information of the processing device to be output to the processing device through the connecting section, the gain setting information being information for setting the gain of the programmable gain amplifier of an analog front-end section that the processing device has to perform signal processing to a signal received from the ultrasonic element array.

2. The head unit according to claim 1, wherein the storing section stores the gain setting information further for setting gain of a low noise amplifier of the analog front-end section as the operation setting information.

3. The head unit according to claim 2, wherein the storing section is configured to store frequency characteristic setting information for setting frequency characteristics of a low-pass filter of the analog front-end section as the operation setting information.

4. The head unit according to claim 1, wherein the storing section is configured to store the operation setting information corresponding to a probe target of the ultrasonic probe.

5. The head unit according to claim 4, wherein the operation setting information corresponding to the probe target of the ultrasonic probe corresponds to one of ultrasonic diagnosis image processing and blood pressure measurement processing.

6. The head unit according to claim 1, further comprising a supporting member supporting the element chip and the storing section.

7. The head unit according to claim 6, wherein the connecting section has a plurality of connecting terminals connected to the probe main body,
the storing section and the connecting terminals are disposed on a first surface side of the supporting member, and
the element chip is supported on a second surface side of the supporting member, the second surface being a reverse surface of the first surface of the supporting member.

8. The head unit according to claim 7, wherein the connecting section has a connector including the connecting terminals and a flexible printed circuit board including wiring connecting the connector and the element chip, and
the storing section is disposed in the flexible printed circuit board.

9. An ultrasonic probe comprising:
the probe main body; and
the head unit according to claim 1, the head unit being removably coupled to the probe main body.

10. The ultrasonic probe according to claim 9, wherein the probe main body includes
a processing device having an analog front-end section configured to perform signal processing to a signal received from the ultrasonic element array,
a transmitting section configured to output a driving signal to the ultrasonic element array, and
a controlling section configured to control the analog front-end section and the transmitting section, the controlling section being configured to set operations of the analog front-end section and the transmitting section based on the operation setting information read out from the storing section of the head unit.

11. An electronic instrument comprising:
the head unit according to claim 1.

12. A diagnostic device comprising:
the head unit according to claim 1; and
a display section configured to display image data.

13. The head unit according to claim 3, wherein the frequency characteristic setting information has a value of cutoff frequency.

14. An electronic instrument comprising:
the head unit according to claim 1; and
the probe main body,
the head unit being removably coupled to the probe main body.

15. A diagnostic device comprising:
the head unit according to claim 1;
a probe main body; and
a display section configured to display image data,
the head unit being removably coupled to the probe main body.

* * * * *